United States Patent [19]

Basilico et al.

[11] Patent Number: 5,459,250

[45] Date of Patent: Oct. 17, 1995

[54] TRUNCATED MAMMALIAN GROWTH FACTOR DNA SEQUENCE

[75] Inventors: Claudio Basilico; Daniela Talarico, both of New York, N.Y.

[73] Assignee: New York University, New York, N.Y.

[21] Appl. No.: 187,780

[22] Filed: Jan. 25, 1994

Related U.S. Application Data

[63] Continuation of Ser. No. 901,705, Jun. 22, 1992, abandoned, which is a continuation-in-part of Ser. No. 806,771, Dec. 6, 1991, which is a continuation of Ser. No. 177,506, Apr. 4, 1988, abandoned, which is a continuation of Ser. No. 62,925, Jun. 16, 1987, abandoned.

[51] Int. Cl.$^6$ .................................................. C12N 15/18
[52] U.S. Cl. ........................................... 536/23.5; 530/399
[58] Field of Search .............................................. 536/23.5

[56] References Cited

U.S. PATENT DOCUMENTS

| | | | |
|---|---|---|---|
| 4,444,760 | 4/1984 | Thomas | 530/399 |
| 4,716,102 | 12/1987 | Levy | 435/235 |
| 5,126,323 | 6/1992 | Rogers et al. | 514/12 |

FOREIGN PATENT DOCUMENTS

WO8607595 12/1986 WIPO.

OTHER PUBLICATIONS

Moscatelli et al., *Fed. Proc.*, 45:1718, 1986.
Abraham et al., *Science*, 233:545–548, 1986.
Gimenez–Gallego et al., *Biochem. Biophys. Res. Comm.*, 135:611–617, 1986.
Sakamoto et al., *Proc. Natl. Acad. Sci.*, 83:3997–4001, 1986.
Taira, et al., *Proc. Natl. Acad. Sci.*, 84:2980–2984, 1987.
Rueger et al., *Antibiot. Chemother. (Basel)*, 32:43–7, 1984 (abstract only).
Boldogh et al., *Int. J. Cancer*, 28:469–474, 1981 (abstract only).
Abraham et al., *EMBO J.*, 5:2523–2528, 1986.
Esch et al., *Proc. Natl. Sci. USA*, 82:6507–6511, 1985.
Delli-Bovi et al., *Cell*, 50:729–735, 1987.
Delli-Bovi et al., *Proc. Natl. Acad. Sci.*, 84:5660–5664, 1987.
Delli-Bovi et al., *Mol. and Cell. Bio.*, 8:2933–2941, 1988.
Huebner et al., *Onc. Res.*, 3:263–270, 1988.
Quarto et al., *Onc. Res.*, 5:101–110, 1989.
Velcich et al., *Onc. Res.*, 5:31–37, 1989.
Basilico et al., *Annals of N.Y. Acad. Sci.*, 567:95–103, 1989.
Kaner et al., *Science*, 248:1410–1413, 1990.
Mansukhani et al., *Proc. Natl. Acad. Sci.*, 87:4222–4225, 1990.
Talarico et al., *Proc. Natl. Acad. Sci.*, 87:4222–4225, 1990.
Curatola et al., *Mol. and Cell. Bio.*, 10:2475–2484, 1990.
Talarico et al., *Mol. and Cell. Bio.*, 11:1138–1145, 1991.
Mansukhani et al., *Proc. Natl. Acad. Sci.*, 89:3305–3309, 1992.

*Primary Examiner*—Marianne P. Allen
*Attorney, Agent, or Firm*—Darby & Darby

[57] ABSTRACT

A truncated mammalian growth factor, displaying homology to both basic and acidic fibroblast growth factor in a single polypeptide, is disclosed herein. The growth factor is substantially smaller (i.e. has fewer amino acid residues) than the full-length mammalian growth factor, has a higher affinity for fibroblast growth factor receptors than full-length K-FGF and basic fibroblast growth factor and increased mitogenic activity. Also disclosed herein are DNA sequences encoding the truncated growth factor, pharmaceutical formulations containing the truncated growth factor and methods to heal burns and wounds in a mammal by administering the pharmaceutical formulations.

1 Claim, 8 Drawing Sheets

```
                                                              A
                                                              ↓
  1   MSGPGTAAVALLPAVLLALLAPWAGRGGAAAPTAPNGTLEAELERRWESL        50
                          ‾‾‾‾‾‾‾‾‾‾‾‾↑↑***

51   VALSLARLPVAAQPKE⌐AAVQSGAGDYLLGIKRLRRLYCNVGIGFHLQALP      100

101   DGRIGGAHADTRDSLLELSPVERGVVSIFGVASRFFVAMSSKGKLYGSPF       150

151   FTDECTFKEILLPNNYNAYESYKYPGMFIALSKNGKTKKGNRVSPTMKVT       200

201   HFLPRL 206
```

*FIG. 1*

TRUNCATED MAMMALIAN GROWTH FACTOR DNA SEQUENCE

The United States Government has rights to this invention by virtue of grant No. CA42568 from The National Cancer Institute. This is a continuation of application Ser. No. 07/901,705, filed Jun. 22, 1992, now abandoned, which in turn is a continuation-in-part of Ser. No. 07/806,771 filed Dec. 6, 1991, which in turn is a continuation of Ser. No. 07/177,506 filed Apr. 4, 1988, now abandoned, which in turn is a continuation of Ser. No. 07/062,925 filed Jun. 16, 1987, now abandoned.

FIELD OF THE INVENTION

This invention pertains to a mammalian growth factor, pharmaceutical formulations comprising said factor and methods for healing wounds or burns in mammals comprising administering said formulations.

BACKGROUND OF THE INVENTION

This invention pertains to a novel polypeptide having mammalian growth factor activity and to methods for using it.

A variety of diffusible factors which stimulate the growth of cells in a hormone-like manner are generally called "growth factors". Growth factors are often present in serum and have also been isolated from a variety of organs. They are protein molecules (or groups of such molecules) and in all known cases they interact with specific cell surface receptors to promote cellular growth and/or differentiation. Growth factors vary in their tissue specificity, i.e. some interact only with specific cell types, while others are active on a wider cell type range.

Among the best known groups of mammalian growth factors are: (1) platelet derived growth factor (PDGF), released from platelets; (2) epidermal growth factor (EGF); (3) hematopoietic growth factors (including interleukins 1, 2, and 3), required for growth and differentiation of lymphocytes, and colony stimulating factors (CSF), promoting growth and differentiation of hematopoietic stem cells; (4) angiogenic (literally "blood-vessel-forming") growth factors, such as the fibroblast growth factors (FGF) believed to promote growth and organization of endothelial cells into new blood vessels; (5) miscellaneous growth factors released by tumor cells.

Two well-characterized angiogenic factors are basic and acidic fibroblast growth factors (FGF), believed to be most important in Vivo for endothelial cell growth. However, neither basic FGF nor acidic FGF has proven useful as pharmaceutical agents for promotion of wound healing. Several factors may contribute to the unsuitability of basic FGF and acidic FGF as pharmaceutical agents. Neither factor is sufficiently stable for effective pharmaceutical formulation. Basic FGF demonstrates restricted interaction with FGF receptors in vitro, and thus cannot be expected to interact with all FGF receptors in vivo. Finally, basic FGF and acidic FGF have thus far proven ineffective in animal models.

Co-pending U.S. patent application Ser. No. 07/806,791 filed Dec. 6, 1991 discloses an angiogenic mammalian growth factor isolated from Kaposi's Sarcoma cells and having substantial homology to each of acidic and basic fibroblast growth factor in a single polypeptide. The growth factor protein comprises 176 amino acid residues and is a mature (secreted) glycoprotein. This growth factor has variously been called K-FGF or FGF-4, and it has shown promising results as a wound healing agent in preclinical studies in an ischemic rabbit ear model. In such a model, K-FGF promoted wound healing better than basic or acidic FGF.

Growth factors are believed to promote wound healing. For example, EGF present in saliva is believed to accelerate wound healing in mice. Schultz G.S et al. (*Science* 232:350–352, 1986) report that transforming growth factor (TGF)-alpha and vaccinia virus growth factor (VGF), both of which are substantially homologous to EGF, accelerated epidermal wound healing in pigs when topically applied to second degree burns and were significantly more active than EGF.

Of the above-mentioned growth factors, the angiogenic growth factors would be particularly useful as wound healing agents because of their ability to promote the formation and growth of new blood vessels.

OBJECTS OF THE INVENTION

It is an object of the present invention to provide a novel growth factor useful as a wound healing agent in mammals.

Another object of the present invention is to provide a mammalian growth factor with increased biologic activities.

Yet another object of the present invention is to provide novel pharmaceutical formulations and methods for promoting wound healing in mammals.

A still further object of the present invention is to provide a truncated mammalian growth factor protein having substantial homology to each of acidic and basic fibroblast growth factor protein in a single polypeptide and having substantially higher specific activity than K-FGF protein.

SUMMARY OF THE INVENTION

The present invention pertains to a previously unknown form of truncated mammalian growth factor protein having substantial homology to each of basic and acidic fibroblast growth factor proteins in a single polypeptide chain, said truncated mammalian growth factor being substantially smaller than the full-length mammalian growth factor (the truncated protein is hereinafter referred to as truncated K-FGF or K-FGF-140).

In another aspect, the present invention provides a polypeptide having the amino acid sequence (SEQ. ID. NO. 1):

```
Ala Ala Val Gln Ser Gly Ala Gly Asp Tyr Leu Leu Gly Ile Lys Arg
 1            5               10                   15
Leu Arg Arg Leu Tyr Cys Asn Val Gly Ile Gly Phe His Leu Gln Ala
           20              25              30
Leu Pro Asp Gly Arg Ile Gly Gly Ala His Ala Asp Thr Arg Asp Ser
        35              40              45
```

-continued

| | | | | | | | | | | | | | | |
|---|---|---|---|---|---|---|---|---|---|---|---|---|---|---|
| Leu | Leu | Glu | Leu | Ser | Pro | Val | Glu | Arg | Gly | Val | Val | Ser | Ile | Phe | Gly |
| | 50 | | | | 55 | | | | | 60 | | | | | |
| Val | Ala | Ser | Arg | Phe | Phe | Val | Ala | Met | Ser | Ser | Lys | Gly | Lys | Leu | Tyr |
| 65 | | | | | 70 | | | | | 75 | | | | | 80 |
| Gly | Ser | Pro | Phe | Phe | Thr | Asp | Glu | Cys | Thr | Phe | Lys | Glu | Ile | Leu | Leu |
| | | | | 85 | | | | | 90 | | | | | 95 | |
| Pro | Asn | Asn | Tyr | Asn | Ala | Tyr | Glu | Ser | Tyr | Lys | Tyr | Pro | Gly | Met | Phe |
| | | | 100 | | | | | 105 | | | | | 110 | | |
| Ile | Ala | Leu | Ser | Lys | Asn | Gly | Lys | Thr | Lys | Lys | Gly | Asn | Arg | Val | Ser |
| | | 115 | | | | | 120 | | | | | 125 | | | |
| Pro | Thr | Met | Lys | Val | Thr | His | Phe | Leu | Pro | Arg | Leu. | | | | |
| | 130 | | | | | 135 | | | | | 140 | | | | |

In yet another aspect, the present invention provides a pharmaceutical formulation for treating a mammal suffering from wounds or burns comprising truncated K-FGF and a pharmaceutically acceptable carrier or diluent.

A still further aspect of the present invention involves a method for healing wounds or burns in a mammal in need of such treatment by administration of an effective amount for wound or burn healing of truncated K-FGF.

A still further aspect of the present invention provides an isolated DNA having the sequence (SEQ. ID. NO. 2):

| | | | | | | | | | | | | |
|---|---|---|---|---|---|---|---|---|---|---|---|---|
| GCG | GCC | GTC | CAG | AGC | GGC | GCC | GGC | GAC | TAC | CTG | CTG | GGC | 39 |
| ATC | AAG | CGG | CTG | CGG | CGG | CTC | TAC | TGC | AAC | GTG | GGC | ATC | 78 |
| GGC | TTC | CAC | CTC | CAG | GCG | CTC | CCC | GAC | GGC | CGC | ATC | GGC | 117 |
| GGC | GCG | CAC | GCG | GAC | ACC | CGC | GAC | AGC | CTG | CTG | GAG | CTC | 156 |
| TCG | CCC | GTG | GAG | CGG | GGC | GTG | GTG | AGC | ATC | TTC | GGC | GTG | 195 |
| GCC | AGC | CGG | TTC | TTC | GTG | GCC | ATG | AGC | AGC | AAG | GGC | AAG | 234 |
| CTC | TAT | GGC | TCG | CCC | TTC | TTC | ACC | GAT | GAG | TGC | ACG | TTC | 273 |
| AAG | GAG | ATT | CTC | CTT | CCC | AAC | AAC | TAC | AAC | GCC | TAC | GAG | 312 |
| TCC | TAC | AAG | TAC | CCC | GGC | ATG | TTC | ATC | GCC | CTG | AGC | AAG | 351 |
| AAT | GGG | AAG | ACC | AAG | AAG | GGG | AAC | CGA | GTG | TCG | CCC | ACC | 390 |
| ATG | AAG | GTC | ACC | CAC | TTC | CTC | CCC | AGG | CTG | TGA | | | 423 |

A still further aspect of the present invention provides a truncated K-FGF protein characterized by (i) a molecular weight of about 14,000 Daltons; and (ii) an average FGF-receptor binding affinity of about $9.5 \times 10^{-11}$M.

These and other aspects of the present invention will be apparent to those of ordinary skill in the art in light of the present description, claims and drawings.

BRIEF DESCRIPTION OF THE DRAWINGS

FIG. 1 is a diagram depicting the amino acid sequence of the full-length K-FGF protein and the amino acid sequence of the truncated protein of the present invention, K-FGF-140.

DETAILED DESCRIPTION OF THE INVENTION

Figure 2:
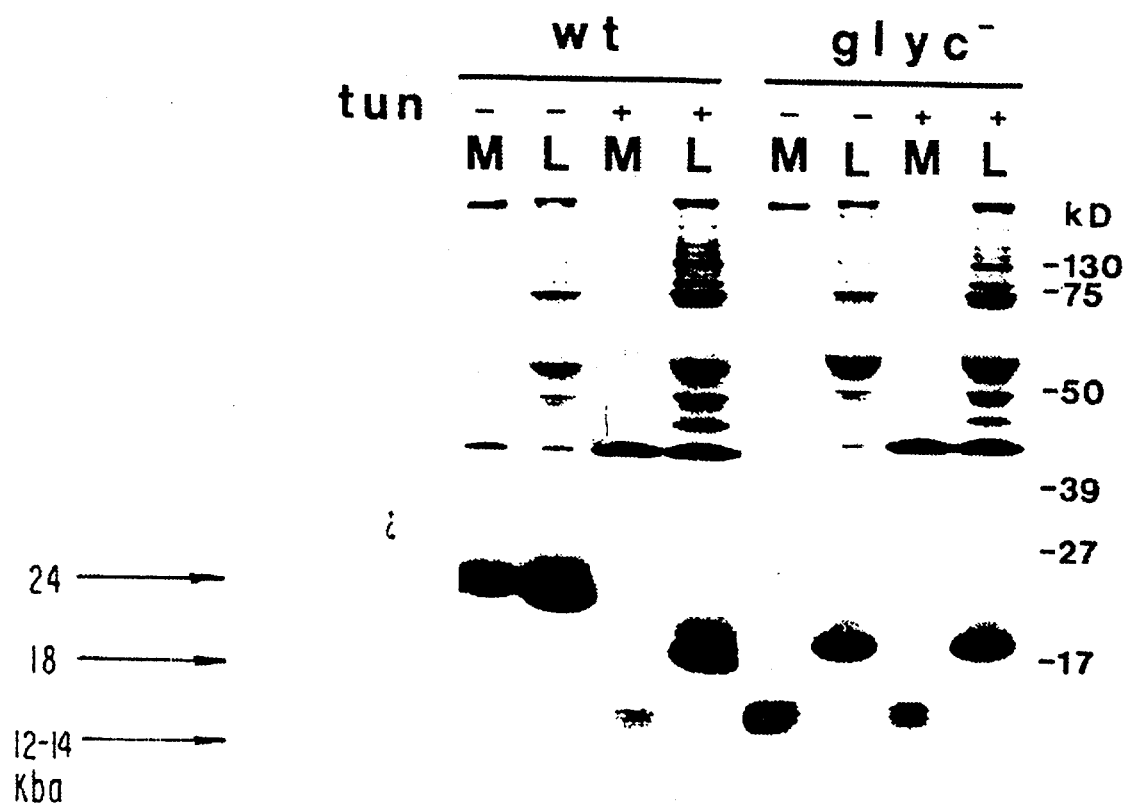
FIG. 2 is an autoadiograph of a sodium dodecyl sulfate polyacrylamide gel electrophoretic (SDS-PAGE) analysis of immunoprecipitated K-FGF forms produced in COS cells transfected with either wild type K-FGF or K-FGF-140 DNA or with a mutated K-FGF cDNA which expresses an unglycosylated form of K-FGF that is processed to produce K-FGF-140.

All patent applications, patents and literature references mentioned in the specification are incorporated by reference in their entirety. In the case of inconsistencies, the present disclosure, including definitions, shall prevail.

The present inventors have surprisingly found a truncated form of the K-FGF protein which demonstrates substantially increased activity over that of either full-length K-FGF, basic FGF, or acidic FGF. The truncated K-FGF protein is not glycosylated and is substantially smaller (i.e. has fewer amino acid residues) than the full-length K-FGF protein. The truncated protein has a higher affinity for fibroblast growth factor receptors than either the mature, full-length K-FGF protein or bFGF. In addition, the truncated protein has a higher affinity for heparin than full-length K-FGF and increased mitogenic (i.e. growth promoting) activity. It is expected that, due to these increased biological activities, the truncated protein of the present invention will also have increased wound healing activity.

"Substantially smaller" refers to the fact that the truncated K-FGF protein of the invention contains about 140 amino acid residues as contrasted with the 176 amino acid residues that are present in the full-length mature, secreted K-FGF protein.

"K-FGF-140" is defined herein as the unglycosylated, truncated mammalian growth factor protein of the present invention.

"K-FGF" is defined herein as the full-length mature human growth factor having a molecular weight of about 18,000 Daltons (non-glycosylated) comprising 176 amino acid residues as disclosed in U.S. patent application Ser. No.

on the K-FGF molecule that are very susceptible to cleavage by cellular proteases located on the cell surface. Thus the protein is cleaved to produce these smaller forms as soon as it becomes externalized. It has been determined that the 14,000 Dalton species is K-FGF-140, a truncated form of the full-length K-FGF protein.

K-FGF-140 retains the same regions of homology to acidic and basic FGF as the full-length K-FGF protein (as shown in Table 1 below) but has increased biological activity.

TABLE 1

BOVINE BASIC FIBROBLAST GROWTH FACTOR

67'AAQPKEAAVQSGAGDYLLG—IKRLRRLYCNVGIGFHLQALPDGRIGGAHADTRDSL—LEL

1"  P A  L P E DGGS GAF P P GHF KDP KRL Y CKNG—GF F L RI  HP DGR VDGVREKS DP HI  KL QL

119'SPVERGVVSIFGVASRFFVAMSSKGKLYGSPFFTDECRFKEILLPNNYNAYESYKYPGMF

56"  Q A E E R GV V S  I  KGV C ANR Y L AMKEDGRLL AS KC VT DEC F F F ERL ES NNYNT Y RS RKY S S WY

179'IALSKNGKTKKGNRVSPTMKVTHFLPRL

116"  V AL KRT GQ Y KL GP KT GP GQ KA I  LF L P MS AKS

BOVINE ACIDIC FIBROBLAST GROWTH FACTOR

67'AAQPKEAAVQSGAGDYLLGIKRLRRLYCNVGIGFHLQALPDGRIGGAHADTRDSL—LELS

1"  F NL P L GNY KKP KLL Y CS  NG—GY F L RI  L P DGT VDGT KDRS  DQHI  QL QL C

120'PVERGVVSIFGVASRFFVAMSSKGKLYGSPFFTDECTFKEILLPNNYNAYESYKYPGM——

48"  AES I GE VYI  KS  TET GQ F L AMDT DGLL Y GS QT P NEE CL F L ERL EENHYNT YI  S  KKHAEKHW

178'FIALSKNGKTKKGNRVSPTMKVTHFLPRL

108"  F V GL KKNGR S  KL GP R T HF GQ KAI  L F L P L P VS S D

A = Ala; R = Arg; N = Asn; D = Asp; C = Cys; Q = Gln; E = Glu; G = Gly; H = His; I = Ile; L = Leu; K = Lys; M = Met; F = Phe; P = Pro; S = Ser; T = Thr; W = Trp; Y = Tyr; V = Val.

07/806,791 filed Dec. 6, 1991.

"Mitogenic activity" in reference to the biological activity of the truncated protein of the present invention is defined herein as the ability of the protein to induce DNA synthesis and proliferation of cells in culture.

"Substantial homology to each of acidic and basic fibroblast growth factors" is defined herein as having regions of identity (either exact or by conservative substitution) to said growth factors as shown in Table 1 below.

K-FGF-140 was discovered during studies on the effect of glycosylation on the secretion of full-length K-FGF. Simian COS cells that were transfected with a plasmid encoding the full-length human K-FGF protein and incubated with tunicamycin (an inhibitor of N-linked glycosylation), accumulated an unglycosylated K-FGF protein within the cells of approximately 18,000 Daltons (the expected size of the unglycosylated full-length K-FGF protein). Surprisingly, only proteins of 12,000– 14,000 Daltons were detected in the culture medium (i.e. were secreted). This was more clearly shown using a K-FGF cDNA mutated in such a way to express a protein in which amino acid 38 (Threonine) of the full length K-FGF precursor protein was replaced by Alanine. This protein cannot be glycosylated. COS cells transfected with a plasmid encoding this mutated form of K-FGF also accumulate within the cells an unglycosylated K-FGF protein of approximately 18,000 daltons, but produce in the medium only forms of 12,000–14,000 daltons. Apparently, the removal of the sugar residues exposes sites In Table 1, the N-terminal amino acid (alanine) of K-FGF-140 is residue 67 of the full-length K-FGF protein. Two dots between a particular set of amino acid residues indicate exact identity between the truncated growth factor of the present invention and either one of basic (SEQ. ID. NO. 3) and acidic FGF (SEQ. ID. NO. 4), and one dot indicates that there has been a conservative substitution, e.g. substitution of the same type of amino acid such as phenyl-alanine substituted for tyrosine. In addition, the amino acid sequence of the truncated growth factor of the present invention are number 67'–206', while the FGF sequences are presented as 1"–146" and 1"–141" for basic and acidic FGF, respectively. That is to say residues 1"–146" comprise the sequence of basic FGF, while residues 1"–141" comprise acidic FGF.

As shown in Example 5 below, the truncated protein had mitogenic activity that is 4–5 times greater (i.e. increased DNA synthesis and cell proliferation activity) than the full-length K-FGF protein as shown by its ability to induce proliferation of 3T3 cells at concentrations 4–5 times lower than those of K-FGF. The truncated K-FGF protein also has a higher affinity for two of the FGF receptors than either the full-length K-FGF protein or basic fibroblast growth factor (bFGF).

The growth factor of the present invention can be obtained from the medium of cells transfected or transformed by the "wild type" or full-length K-FGF gene that have been cultivated in the presence of glycosylation inhibitors, such as tunicamycin. Alternatively, K-FGF-140 can be obtained from the medium of cells transfected or transformed by a mutated K-FGF cDNA that produces a protein incapable of being glycosylated, as the one described above, or preferably by using a suitable DNA construct to transform or transfect a eukaryotic, plant, or bacterial cell (e.g. *E. coli*), the latter described in Example 2 below. The wild type full-length gene can be obtained as described in co-pending U.S. patent application Ser. No. 7/806,791 filed Dec. 6, 1991. Alternatively the DNA sequence can be used to chemically synthesize the K-FGF-140 gene using techniques well known in the art.

The DNA encoding the growth factor of the present invention can be cloned and the protein can be expressed in any eukaryotic or prokaryotic system known in the art. Non-limiting examples of suitable eukaryotic expression systems include yeast expression vectors (described by Brake, A. et al., *Proc. Nat. Acad. Sci.* USA 81: 4642–4646, 1984), Polyoma virus based expression vectors (described in Kern, F. G. et al. *Gene* 43: 237–245, 1986) Simian virus 40 (SV40)-based expression vectors in COS-1 Simian cells (as described in Gerbing, M.J. et al. *Nature* 293: 620–625, 1981) and baculovirus (insect)-based expression vectors (described in U.S. Pat. No. 4,745,051, issued May 17, 1988 and U.S. Pat. No. 4,879,232, issued Nov. 7, 1989). An example of a procaryotic expression system (e.g. *E. coli*) is presented below in Example 2 and an example of a eukaryotic expression system (e.g. COS cells) is presented below in Example 3. Particularly preferred expression vectors include *E. coli*, simian COS cells and baculovirus (insect) cells.

The DNA encoding the truncated mammalian growth factor of the present invention may be modified without changing the primary sequence of the encoded polypeptide in order to increase the efficiency of its production. One such example is presented in Example 2 below where AT nucleotides were incorporated into the 5' end of the molecule for cloning into *E. coli*. In addition, an ATG encoding methionine, was also added to the 5' end of the DNA. Other modifications for cloning and expression in other systems are known in the art and are within the scope of the present invention.

The DNA sequence (SEQ. ID. NO. 5) of K-FGF-140 is as follows:

```
GCGGCCGTCCAGAGCGGCGCCGGCGACTACCTGCTGGGC39
Ala  Ala  Val  Gln  Ser  Gly  Ala  Gly  Asp  Tyr  Leu  Leu  Gly
 1              5                         10

ATCAAGCGGCTGCGGCGGCTCTACTGCAACGTGGGCATC78
Ile  Lys  Arg  Leu  Arg  Arg  Leu  Tyr  Cys  Asn  Val  Gly  Ile
     15                  20                       25

GGCTTCCACCTCCAGGCGCTCCCCGACGGCCGCATCGGC117
Gly  Phe  His  Leu  Gln  Ala  Leu  Pro  Asp  Gly  Arg  Ile  Gly
               30                       35

GGCGCGCACGCGGACACCCGCGACAGCCTGCTGGAGCTC156
Gly  Ala  His  Ala  Asp  Thr  Arg  Asp  Ser  Leu  Leu  Glu  Leu
 40                      45                       50

TCGCCCGTGGAGCGGGGCGTGGTGAGCATCTTCGGCGTG195
Ser  Pro  Val  Glu  Arg  Gly  Val  Val  Ser  Ile  Phe  Gly  Val
           55                      60                       65

GCCAGCCGGTTCTTCGTGGCCATGAGCAGCAAGGGCAAG234
Ala  Ser  Arg  Phe  Phe  Val  Ala  Met  Ser  Ser  Lys  Gly  Lys
                     70                       75

CTCTATGGCTCGCCCTTCTTCACCGATGAGTGCACGTTC273
Leu  Tyr  Gly  Ser  Pro  Phe  Phe  Thr  Asp  Glu  Cys  Thr  Phe
           80                  85                  90

AAGGAGATTCTCCTTCCCAACAACTACAACGCCTACGAG312
Lys  Glu  Ile  Leu  Leu  Pro  Asn  Asn  Tyr  Asn  Ala  Tyr  Glu
                95                 100

TCCTACAAGTACCCCGGCATGTTCATCGCCCTGAGCAAG351
Ser  Tyr  Lys  Tyr  Pro  Gly  Met  Phe  Ile  Ala  Leu  Ser  Lys
105                      110                     115

AATGGGAAGACCAAGAAGGGGAACCGAGTGTCGCCCACC390
Asn  Gly  Lys  Thr  Lys  Lys  Gly  Asn  Arg  Val  Ser  Pro  Thr
          120                     125                     130

ATGAAGGTCACCCACTTCCTCCCCAGGCTGTGA423
Met  Lys  Val  Thr  His  Phe  Leu  Pro  Arg  Leu
                    135                 140
```

The polypeptide of the present invention can be purified by any one of the many techniques that are well known in the art for use in conjunction with the expression system to produce the polypeptide. For example, when expressing the protein in *E. coli*, a purification procedure such as that disclosed in Example 2 below may be used.

The truncated K-FGF mammalian growth factor of the present invention can be employed as a wound-healing agent for various mammalian wounds, such as decubitus ulcers or burns. When employed as a wound or burn healing agent, the growth factor of the present invention may be administered to a mammal in need of such treatment orally, parenterally, or preferably, topically, directly to the affected area in amounts broadly ranging between about 10 nanograms and about 10 micrograms per dose. The number of treatments required to treat a particular wound or burn and the duration of treatment can vary from individual to individual depending upon the severity of the wound or burn. A typical treatment would comprise 1 or 2 topical applications per day, that are applied directly to the surface of the wound or burn.

The growth factor of the present invention can be prepared in pharmaceutical formulations or dosage forms to be used as a wound or burn healing agent. Pharmaceutical formulations containing the mammalian growth factor of the present invention (or physiologically acceptable salts thereof) as at least one of the active ingredients may also contain pharmaceutically-acceptable carriers, diluents, fillers, salts and other materials well-known in the art depending upon the dosage form utilized. For example, parenteral dosage forms may comprise a physiologic, sterile saline solution. Topical dosage forms may comprise for example, lanolin, hydroxymethyl cellulose or propylene glycol. In an alternative embodiment, the mammalian growth factor of the present invention may be mixed with antibiotic creams (such as Silvadene, Marion Laboratories, Kansas City, Mich., Achromycin, Lederle Laboratories, Pearl River, N.Y., or Terramycin, Pfipharmecs, New York, N.Y.) well-known in the art.

As will be understood by those of ordinary skill in the art, the pharmaceutical formulations or dosage forms of the present invention need not contain an effective amount of the truncated protein of the present invention as such effective conditions that allowed tritiated leucine to be incorporated into the expressed protein. The leucine-labeled protein was purified by precipitation with a polyclonal antibody raised against full-length K-FGF. The amino terminus of the purified K-FGF-140 protein was sequenced using a protein sequencer (Applied Biosystems model 470A). Tritium was found in several cycles and these cycles were assigned as leucine residues. There was a major sequence and a minor sequence. By a process of elimination the major sequence was identified as starting at residue 67 of the K-FGF full-length sequence (Delli-Bovi et al. Cell 50: 729– 37 1987, Delli-Bovi et al. 1988 *Molecular and Cellular Biology* 8: 2933–41). The sequence of this truncated protein is illustrated in FIG. 1.

A variety of different expression vectors may be used to produce the K-FGF-140 protein in *E. coli*. A bacterial expression vector was designed and constructed encoding the K-FGF-140 protein under the control of the bacteriophage lambda pL promoter and the cII ribosome binding site.

The full-length cDNA sequence of K-FGF was altered using site directed mutagenesis (T.A. Kunkel et al. (1987) *Methods in Enzymol.*, Vol. 154, pages 367–382) to delete the sequence for the first 66 amino acids and place an initiator methionine in front of residue 67. It was also found desirable to change the codon usage pattern (using site directed mutagenesis) at the start of the truncated sequence to codons containing more Adenine or Thymidine. The sequence changes that were made are illustrated in Table 2 below.

TABLE 2

Original SequenceGCGGCCGTCCAGAGCGGCGCCGGCGAC... SEQ ID NO:6:

New Sequence     ATG GC<u>A</u> GC<u>A</u> GT<u>T</u> CAA <u>T</u>CA GG<u>A</u> GC<u>A</u> GGC GAC ... SEQ ID NO:7:

Amino AcidMetAlaAlaValGlnSerGlyAlaGlyAsp... SEQ ID NO:8:

amounts can be achieved by administering a plurality of formulations or dosage forms.

Although the truncated K-FGF growth factor of the present invention is particularly useful as a wound or burn healing agent it also can be employed as an agent to promote the growth of cells in tissue culture and/or as a partial serum substitute. The growth-promoting properties of truncated K-FGF are illustrated in Example 5 below.

The invention is described further below in specific working examples which are intended to illustrate the present invention without limiting its scope.

EXAMPLE 1

AMINO ACID SEQUENCE OF THE HUMAN K-FGF PRECURSOR PROTEIN

The amino acid sequence of K-FGF and K-FGF-140 are shown in FIG. 1. In FIG. 1, arrows under the sequence indicate the sites of cleavage of the mature, secreted form of K-FGF. Asterisks indicate the glycosylation signal. The result of the mutation introduced in the cDNA to eliminate glycosylation is indicated above the asterisks (Threonine to Alanine). The [sign indicates the site of cleavage which generates K-FGF-140.

EXAMPLE 2

CONSTRUCTION AND EXPRESSION VECTOR FOR K-FGF-140

The K-FGF-140 cDNA (which was mutated at the glycosylation site) was expressed in COS cells using media In Table 2, the nucleotides which were changed are underlined. None of the changes resulted in a change in the amino acids sequence of the protein.

Other changes to more favorable codons or changes further into the sequence could also have been made. This AT rich sequence at the start of the gene was found to optimize the amount of K-FGF-140 protein expressed in *E. coli* B4.

The K-FGF-140 gene was expressed in *E. coli*. Expression of the gene was accomplished by growing cells at 30° C. (the permissive temperature for the temperature sensitive lambda repressor). The culture was then shifted to 40° C. where the lambda repressor fails to repress the pL lambda promoter and maintained at this temperature for 3 hours. Cells were harvested by centrifugation and stored at −80° C. The bacterial cells were broken in the presence of break buffer (6.0 g Tris adjusted to pH 7.0 with HCl, 1.9 g EDTA, 1.7 g PMSF, 1.0 g pABA all in 1 L water) in a homogenizer (Gaulin model 15). The cells were passed three times through the homogenizer at a pressure differential of 8000–9000 pounds per square inch (PSI). The broken cell paste was frozen in liquid nitrogen and stored at −80° C.

Most of the K-FGF-140 protein was found in the insoluble fraction in the cell lysate and was harvested by centrifugation. The growth factor was extracted from the centrifugation pellet by suspension in extraction buffer (50 mM Tris pH 7.5, 200 mM MgCl$_2$). The extract was centrifuged and K-FGF-140 was found in the soluble fraction. This fraction was loaded onto a heparin Toyopearl (Tosohaas) column, and the buffer exchanged with 0.5M NaCl 50 mM Tris pH 7.5 followed by 0.5M NaCl, 20 mM Na phosphate pH 7.5. Finally, the K-FGF-140 protein was eluted with a gradient of 0.5–1.75 NaCl in 20 mM Na phosphate pH 7.5. The protein was found to elute at a salt concentration of about 1.55 M NaCl whereas full-length K-FGF elutes at about 1.15M NaCl.

EXAMPLE 3

IMMUNOPRECIPITATION ANALYSIS OF THE K-FGF FORMS PRODUCED IN COS CELLS TRANSFECTED WITH THE GLYC-K-FGF-140 cDNA

COS cells were transfected with the 91203B expression plasmid (described in Delli-Bovi et al. (1987) Cell, Vol. 50, pages 729–737) containing either the full-length human K-FGF cDNA or a mutated cDNA encoding a protein lacking the N-linked glycosylation signal (glyc(–)cDNA). 40 hours later the cells were labelled with $^{35}S$-methionine for 8 hours, in the presence (+) or absence (–) of tunicamycin, a drug that inhibits N-linked glycosylation. Labelled proteins from either the cell lysate (indicated as L) or medium (indicated as M) were immunoprecipitated with anti-K-FGF rabbit antibodies and electrophoresed on SDS-PAGE. The gel was then subjected to autoradiography. The results are shown in FIG. 2.

In FIG. 2, M.W. markers are indicated on the right. It can be seen that the cell transfected with the glyc(–)cDNA expressed in the cell lysate a protein of apparent M.W. of 18,000 Daltons, identical to the one produced by the wild-type K-FGF DNA in the presence of tunicamycin. This protein cannot however, be detected in the culture medium, where only two bands of MW 12,000–14,000 were seen.

EXAMPLE 4

ELUTION OF K-FGF-140 FROM HEPARIN AFFINITY COLUMNS

Figure 3:
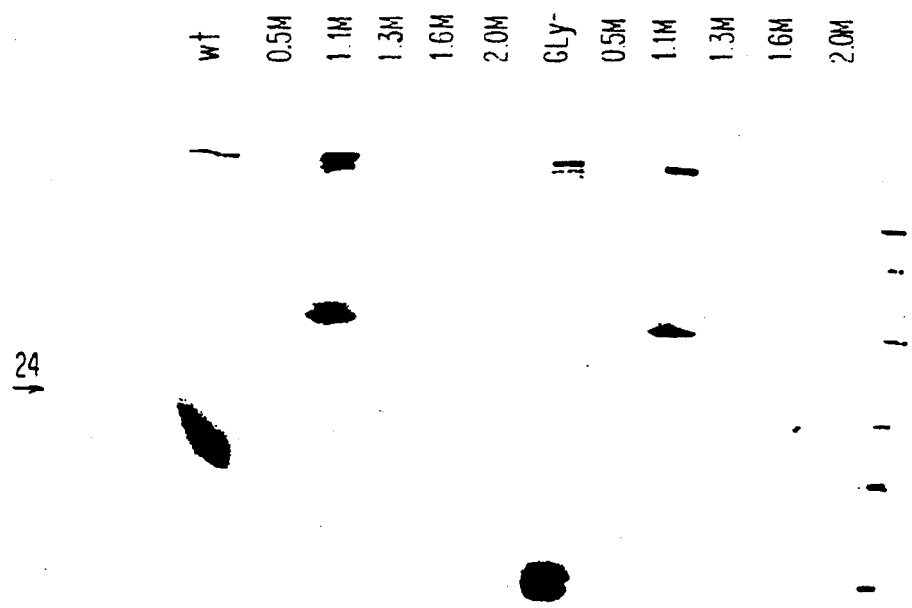
FIG. 3 is an autoradiograph of an SDS-PAGE analysis of the elution of K-FGF and K-FGF-140 from heparin affinity columns.

Conditioned Medium labeled with $^{35}S$-methionine produced from COS cells transfected with either of K-FGF or glyc-cDNAs (i.e. K-FGF-140) was absorbed to Heparin-Sepharose columns and eluted with increasing salt concentrations. Fractions were immunoprecipitated with anti-K-FGF antibodies, and electrophoresed on SDS-PAGE to identify the K-FGF proteins. The results are shown in FIG. 3.

It can be seen that all or most of K-FGF eluted at 1.1M NaCl while the truncated K-FGF forms eluted with a peak at 1.3–1.6M NaCl.

EXAMPLE 5

STIMULATION OF DNA SYNTHESIS IN QUIESCENT BALB/c-3T3 CELLS BY HUMAN RECOMBINANT K-FGF OR BY RECOMBINANT K-FGF-140

BALB/c-3T3 cells were incubated for two days in medium containing 0.5% serum, at which point cells were treated with different concentrations of K-FGF or K-FGF-140. 18 hours later the cells were labeled with $^3H$-thymidine (1 µCi/ml) for 6 hours. Radioactivity incorporated into cellular DNA was counted after trichloroacetic acid (TCA) precipitation. The results are shown in FIG. 4.

Figure 4:
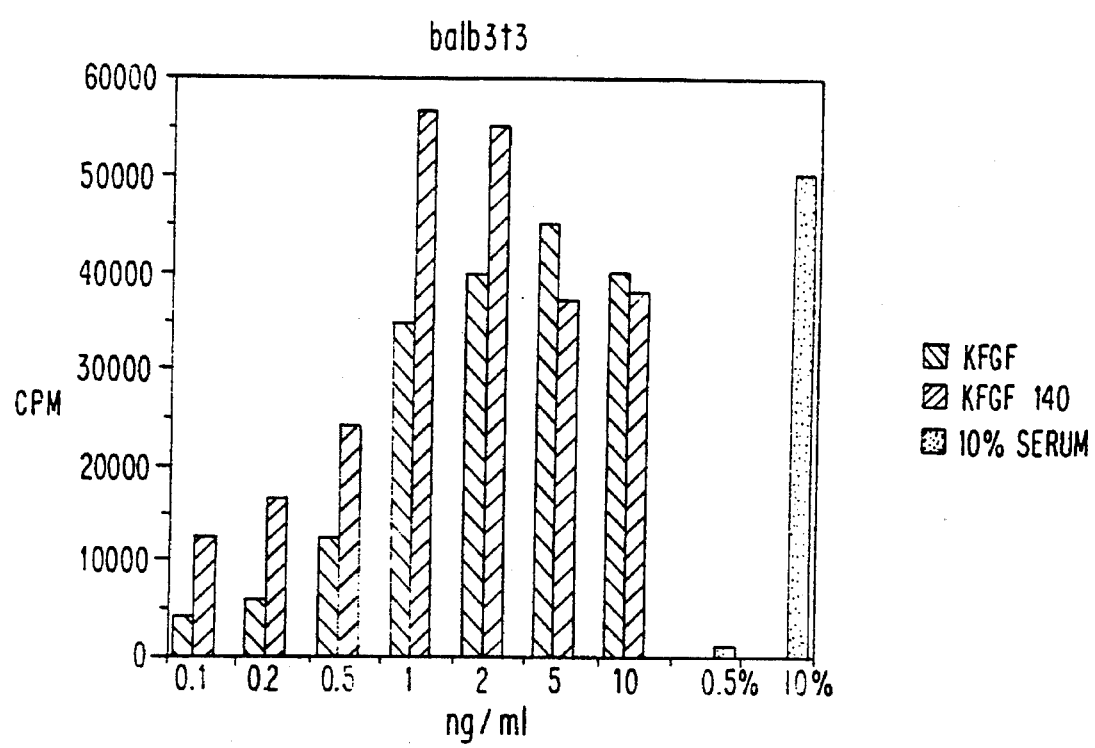
FIG. 4 is a graph showing the stimulation of DNA synthesis in quiescent BALB/c-3T3 cells by recombinant K-FGF and K-FGF-140.
Figure 5A:
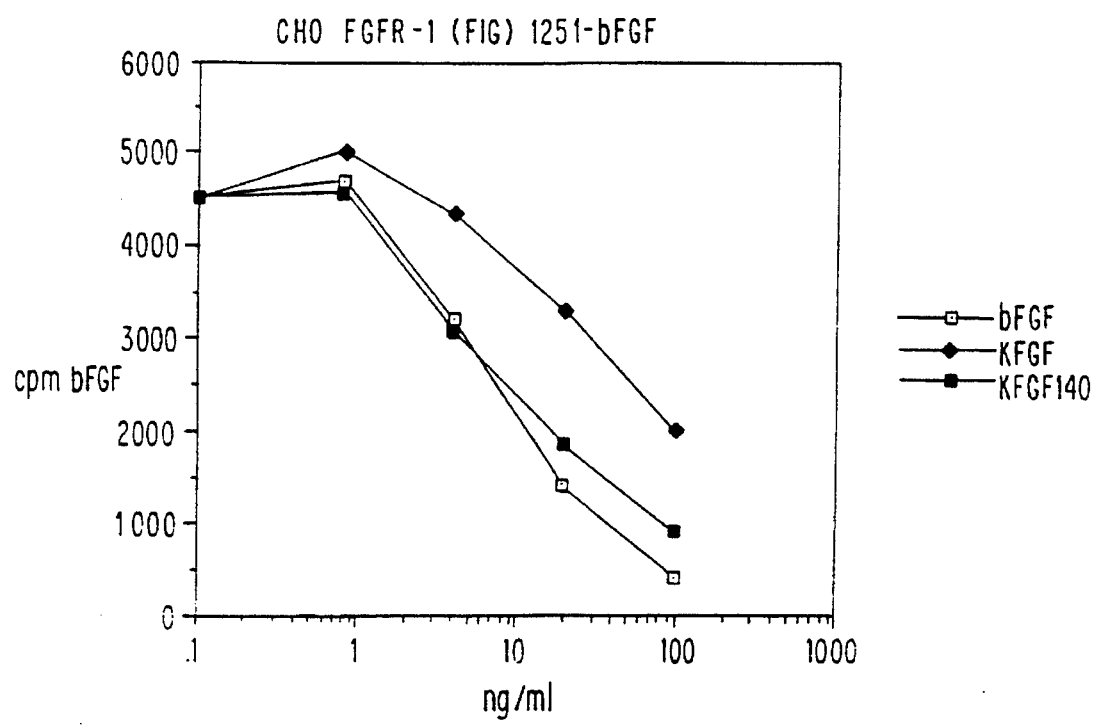
FIGS. 5 (A and B) are graphs depicting a competition assay of the ability of K-FGF and K-FGF-140 to displace labeled basic fibroblast growth factor (bFGF) binding to Chinese Hamster Ovary (CHO) cells expressing the FGF receptor 1 (flg) or 2 (bek).
Figure 5B:
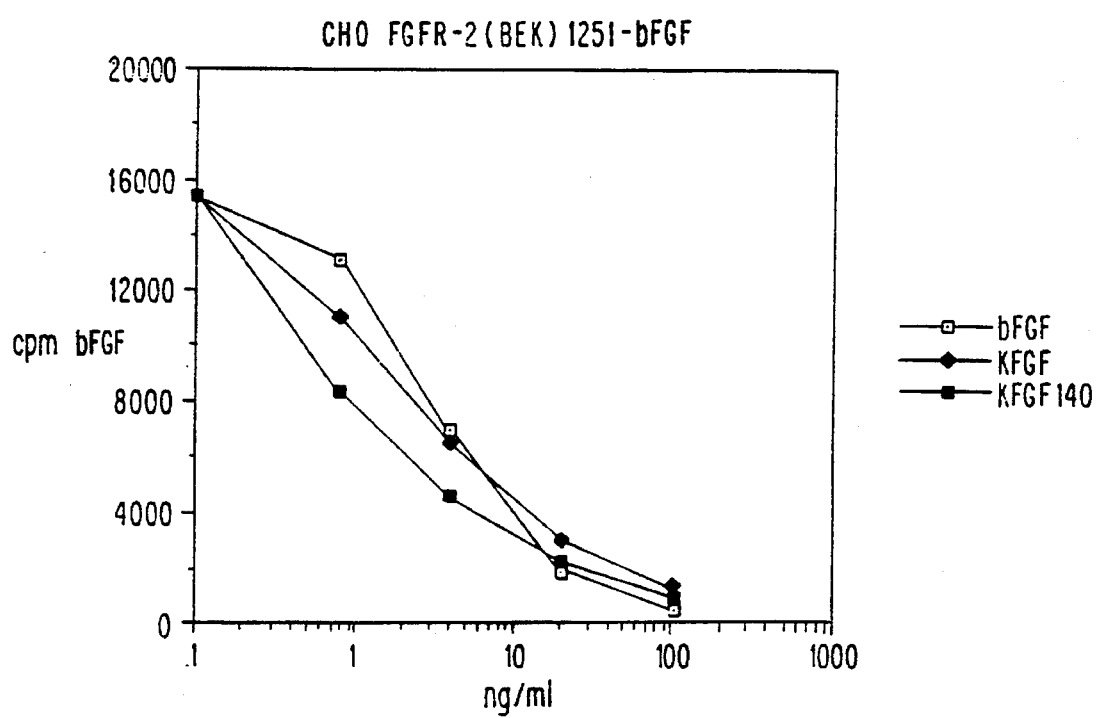

In FIG. 4, 0.5%=negative control, 10%=cells stimulated with 10% serum. As can be seen from the data in FIG. 5, 0.1 ng of K-FGF-140 was capable of producing the same stimulation of DNA synthesis as that of 0.5 ng of K-FGF. Furthermore, maximum stimulation in $^3H$-thymidine uptake occurred using 1ng/ml of K-FGF-140 and 5ng/ml full-length K-FGF. Treatment with 1ng/ml of K-FGF-140 led to a greater amount of cell proliferation than all other additions, including 10% serum.

EXAMPLE 6

RECEPTOR BINDING

To study the affinity of K-FGF-140 for FGF receptors, the ability of K-FGF and K-FGF-140 to compete with $^{125}I$-labeled basic fibroblast growth factor (bFGF) for binding to CHO 4–1 cells expressing FGF receptor-1 (Mansukhani, A. et al. (1992) Proc. Natl, Acad. Sci. USA, Vol. 89, pages 3305–3309) (A) or to CHO 3–7.5 cells expressing the FGF receptor-2 (Mansukhani, A. et al. (1990) Proc. Natl. Acad. Sci. USA, Vol. 87, pages 4378–4382) (B) was performed. Cells ($1\times10^6$ cells/35 mm dish) were incubated at 4° C. with Dulbecco's modified EAGLE's medium (DMEM) containing 0.15% gelatin, 25 mM Hepes (pH 7.4), Heparin (10 µg/ml), $^{125}I$-labeled bFGF (4 ng/ml s.a. $3.2\times10^{17}$ cpm/mole, Collaborative Research) and the indicated concentration of unlabeled bFGF, K-FGF or K-FGF-140. After 2 hours the cells were washed with 2M NaCl buffered at pH 7.4 to remove growth factor bound to the matrix, and with 2M NaCl buffered at pH 4.0 to remove the ligand bound to high affinity receptors. The amount of $^{125}I$-labeled bFGF bound to high affinity receptors was determined. The results are shown in FIG. 5 (A and B).

In the CHO clone expressing the FGF receptor 1 (FIG. 5A) the data show that about 8 times more K-FGF than bFGF or K-FGF-140 was needed to compete for the binding of $^{125}I$-bFGF; in the CHO clone expressing the FGF receptor 2 (FIG. 5B), K-FGF-140 was more efficient than K-FGF and bFGF in competing for the binding of $^{125}I$-labeled bFGF. In this case the affinity of K-FGF-140 for the receptors was about three times higher than that of bFGF or full-length K-FGF.

EXAMPLE 7

COMPETITION BETWEEN K-FGF AND K-FGF-140 FOR RECEPTOR BINDING

Figure 6A:
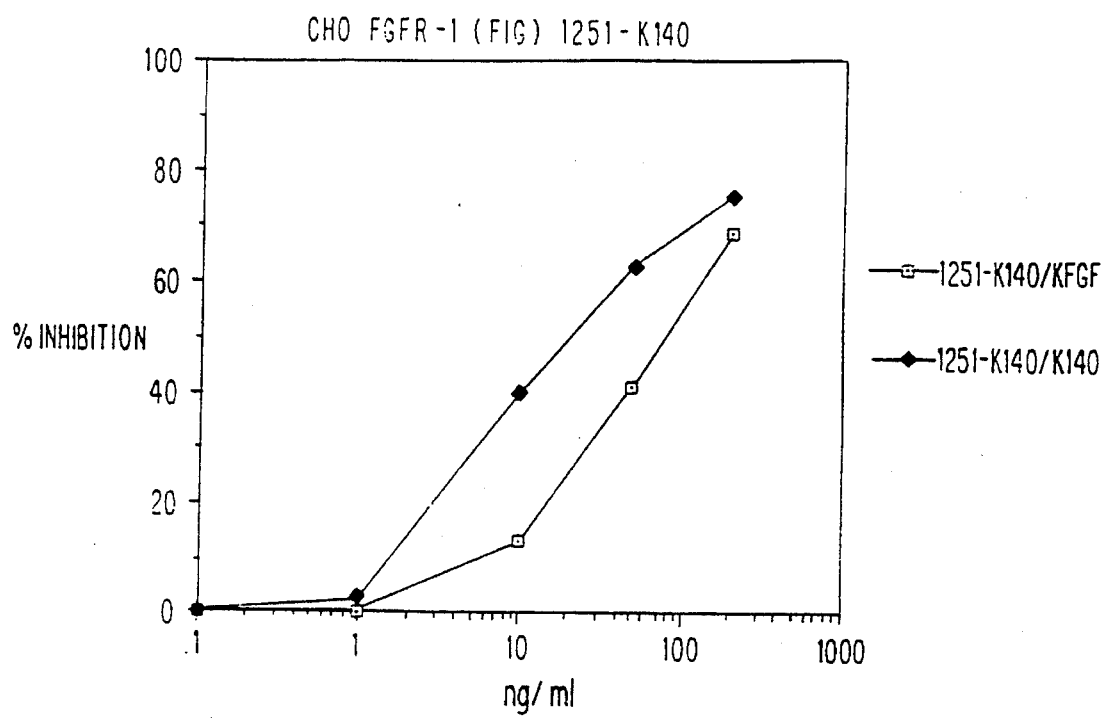
FIG. 6 (A–D) are a series of graphs depicting competition assays between K-FGF and K-FGF-140 for receptors on CHO cells expressing the FGF receptor 1 (flg) or 2 (bek).
Figure 6B:
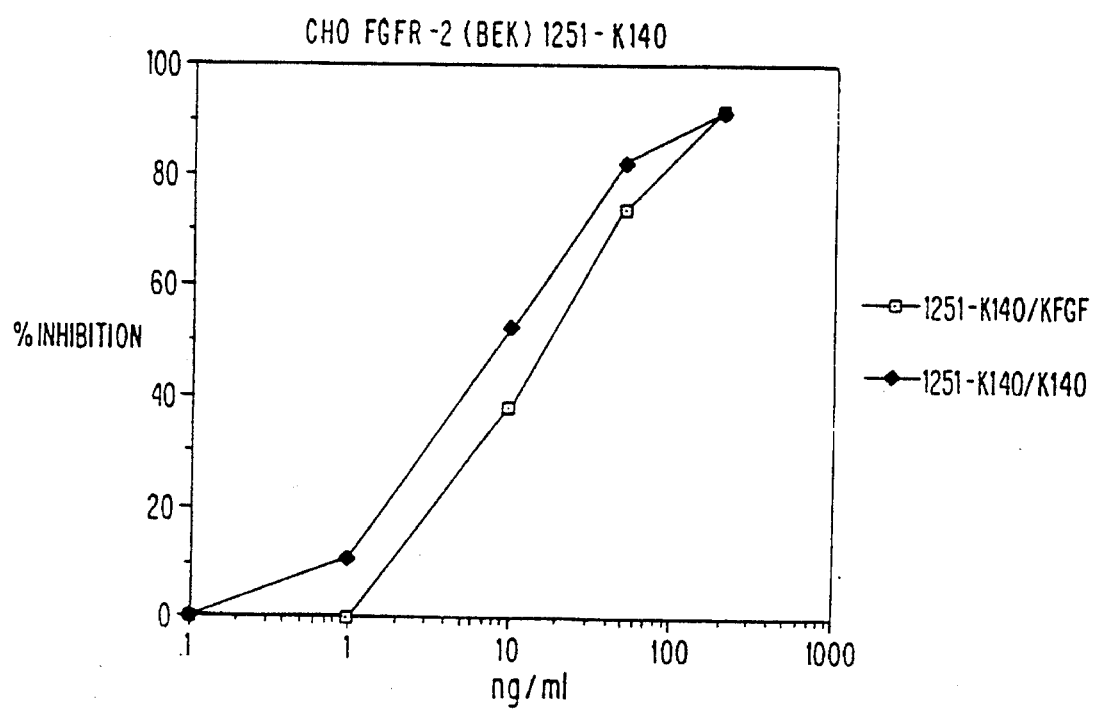
Figure 6C:
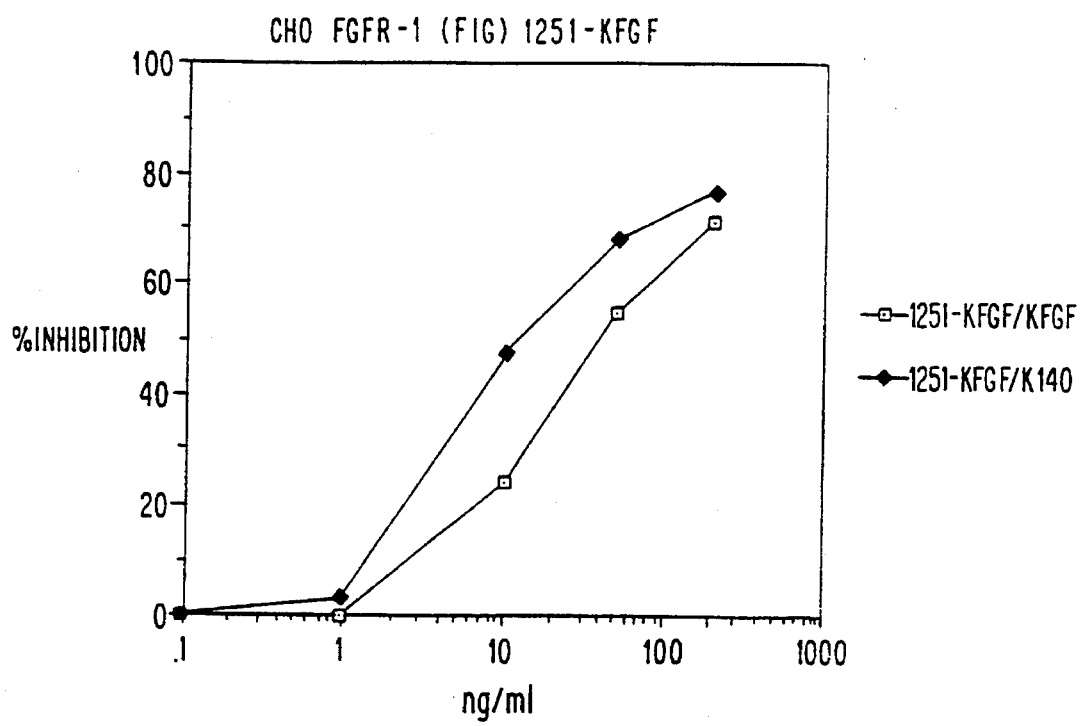
Figure 6D:
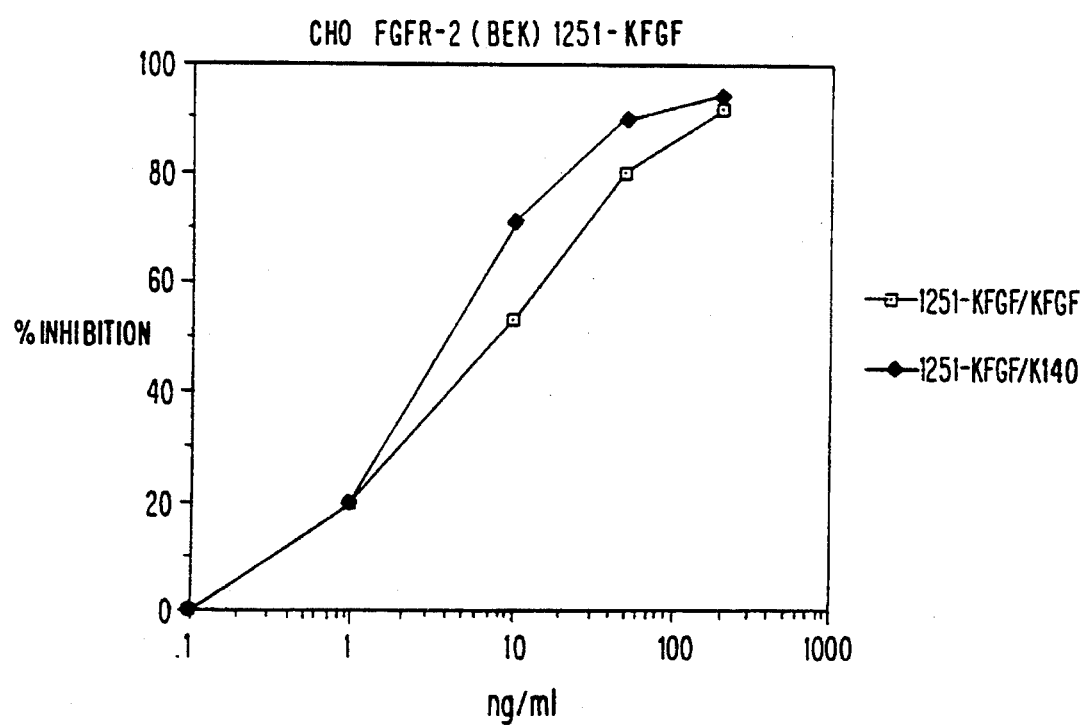

Clones CHO 4–1 expressing FGF receptor-1 (FIG. 6A and FIG. 6C) or CHO 3–7.5 expressing FGF receptor-2 (FIG. 6B and FIG. 6D) were incubated with $^{125}I$-labeled K-FGF-140 (11 ng/ml, specific activity $7.7\times10^{16}$ cpm/mole) (FIG. 6A and B) or with $^{125}I$-labeled K-FGF (8 ng/ml, specific activity $9.9\times10^{16}$ cpm/mole) (FIG. 6C and D), Heparin (10 ug/ml) and the indicated concentration of unlabeled K-FGF or K-FGF-140. After 2 hours at 4° C. the medium was removed, the cells were washed with ice cold Tris and were lysed in 0.6% SDS/50mM.Tris/HCl pH 7.4, 0.15M NaCl, 5 mM.EDTA, and the cell associated radioactivity was determined. The data are expressed as % of inhibition of Iodine labeled growth-factor binding by the indicated amount of unlabeled growth factor.

The data presented in FIG. 6 show that K-FGF-140 had a higher affinity for both FGF (FIGS. 6A and 6C and FIGS. 6B and 6) receptors than full-length K-FGF protein.

EXAMPLE 8

SCATCHARD ANALYSIS OF K-FGF AND K-FGF-140 BINDING TO CHO CELLS EXPRESSING THE FLG RECEPTOR

Scatchard analysis of the binding of K-FGF and K-FGF-140 was performed on CHO 4–1 cells expressing the FGF receptor-1 as follows. Cells at $4.8\times10^5$/35mm dish were incubated at 4° C. with DMEM containing 0.15% gelatin, 25 mM. Hepes(pH 7.4), Heparin (10 ug/ml) and various concentration of $^{125}I$-labeled K-FGF or K-FGF-140 from 0.15 to 20 ng/ml. After 2 hours the medium was removed, the cells were washed with ice cold Tris and $^{125}$I-labeled K-FGF or K-FGF-140 bound to high affinity receptors was removed by extraction in 0.6%SDS/50mMTris/HCl pH 7.4, 0.15 mM NaCl, 5 mM EDTA. Non-specific binding was obtained using the same amount of growth factor on parental CHO DG44 cells that do not express FGF receptors. The results are shown in FIG. 7.

Figure 7:
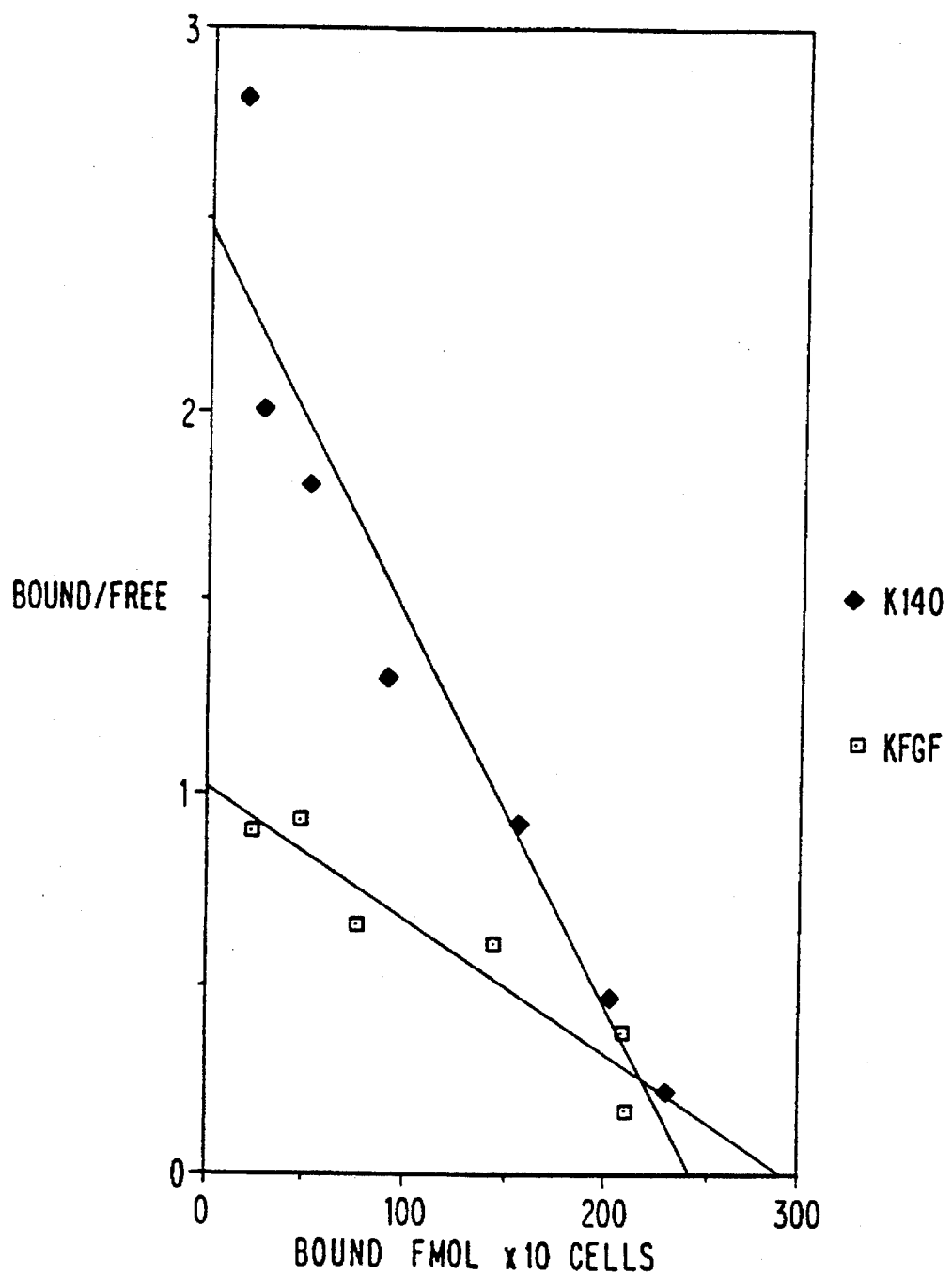
FIG. 7 is a graph depicting a Scatchard analysis of K-FGF and K-FGF-140 binding to CHO cells expressing the FGF receptor 1 (bek).

In FIG. 7, Scatchard analysis of binding to high affinity receptors gave a straight line, indicating a single class of binding sites. The data also indicate that the average binding affinity of K-FGF-140 for the flg receptor is about $9.5 \times 10^{-11}$M or about three times higher than that of full-length K-FGF which has an average binding affinity of about $28.5 \times 10^{-11}$M.

EXAMPLE 9

WOUND HEALING ASSAY

K-FGF-140 will be assayed in an ischemic wound healing system. For this purpose the rabbit ear ischemic model of dermal ulcers, in which healing of these ulcers is retarded because of induced ischemia (reduced blood flow) is used. After wounding (6 mm wounds) K-FGF-140 is applied either in an isotonic buffer or in a gel, applied in a single dose (1–5 µg), and compared to untreated controls, or wounds treated with K-FGF or bFGF. At various days after the beginning of the experiment (up to day 7– 10) the extent of wound healing is determined by measuring a) new epithelium formed at the gap of epithelia tissue at the beginning and end of the experiment) by histological cross sections; b) the gap between the two edges of the granulation tissues; and c) formation of new granulation tissue as measured by staining of immature vs. mature collagen. These techniques are described in Ahn, S. T. and Mustoe, T. A. *Annals Plastic Surgery* 24: 17–23 (1990) and Mustoe, T. A., Pierce G. F., Morishima, C. and Deuel, T.P. *J. Clinical Invest.* 87: 694–703 (1991).

From the in vitro experiments present above showing that K-FGF-140 has higher potency and receptor affinity then K-FGF, it is expected that K-FGF-140 will prove effective at accelerating wound healing in the system, and will prove more potent (effective at lower concentration, faster response) than K-FGF or bKFGF.

---

What is claimed is:

1. An isolated DNA having the sequence (SEQ ID NO:2:):

GCGGCCGTCCAGAGCGGCGCCGGCGAC
TACCTGCTGGGC
ATCAAGCGGCTGCGGCGGCTCTACTGC
AACGTGGGCATC
GGCTTCCACCTCCAGGCGCTCCCCGAC
GGCCGCATCGGC
GGCGCGCACGCGGACACCCGCGACAGC
CTGCTGGAGCTC
TCGCCCGTGGAGCGGGGCGTGGTGAGC
ATCTTCGGCGTG
GCCAGCCGGTTCTTCGTGGCCATGAGC
CTCTATGGCTCGCCCTTCTTCACCGAT
AAGGAGATTCTCCTTCCCAACAACTAC
TCCTACAAGTACCCCGGCATGTTCATC
AATGGGAAGACCAAGAAGGGGAACCGA
ATGAAGGTCACCCACTTCCTCCCCAGG
AGCAAGGGCAAG
GAGTGCACGTTC
AACGCCTACGAG
GCCCTGAGCAAG
GTGTCGCCCACC
CTGTGA.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 140
        ( B ) TYPE: amino acid
        ( C ) STRANDEDNESS: single
        ( D ) TOPOLOGY: linear ( i i ) MOLECULE TYPE:
        ( A ) DESCRIPTION: Protein ( i i i ) HYPOTHETICAL: No ( i v ) ANTI-SENSE: No ( i x ) FEATURE:
        ( A ) NAME/KEY:
        ( B ) LOCATION:
        ( C ) IDENTIFICATION METHOD:
        ( D ) OTHER INFORMATION: This sequence can be
            found on page 4, lines 6-33, in the
            application, as filed.

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 1-140

( x i ) SEQUENCE DESCRIPTION: SEQ ID NO:1:

```
Ala  Ala  Val  Gln  Ser  Gly  Ala  Gly  Asp  Tyr  Leu  Leu  Gly  Ile  Lys  Arg
 1                  5                        10                       15

Leu  Arg  Arg  Leu  Tyr  Cys  Asn  Val  Gly  Ile  Gly  Phe  His  Leu  Gln  Ala
```

|  |  |  |  |  | 20 |  |  |  |  | 25 |  |  |  |  | 30 |  |  |
|---|---|---|---|---|---|---|---|---|---|---|---|---|---|---|---|---|---|
| Leu | Pro | Asp | Gly | Arg | Ile | Gly | Gly | Ala | His | Ala | Asp | Thr | Arg | Asp | Ser |
|  |  |  | 35 |  |  |  |  | 40 |  |  |  |  | 45 |  |  |
| Leu | Leu | Glu | Leu | Ser | Pro | Val | Glu | Arg | Gly | Val | Val | Ser | Ile | Phe | Gly |
|  |  | 50 |  |  |  | 55 |  |  |  |  | 60 |  |  |  |  |
| Val | Ala | Ser | Arg | Phe | Phe | Val | Ala | Met | Ser | Ser | Lys | Gly | Lys | Leu | Tyr |
| 65 |  |  |  |  | 70 |  |  |  |  | 75 |  |  |  |  | 80 |
| Gly | Ser | Pro | Phe | Phe | Thr | Asp | Glu | Cys | Thr | Phe | Lys | Glu | Ile | Leu | Leu |
|  |  |  |  | 85 |  |  |  |  | 90 |  |  |  |  | 95 |  |
| Pro | Asn | Asn | Tyr | Asn | Ala | Tyr | Glu | Ser | Tyr | Lys | Tyr | Pro | Gly | Met | Phe |
|  |  |  | 100 |  |  |  |  | 105 |  |  |  |  | 110 |  |  |
| Ile | Ala | Leu | Ser | Lys | Asn | Gly | Lys | Thr | Lys | Lys | Gly | Asn | Arg | Val | Ser |
|  |  | 115 |  |  |  |  | 120 |  |  |  |  | 125 |  |  |  |
| Pro | Thr | Met | Lys | Val | Thr | His | Phe | Leu | Pro | Arg | Leu |  |  |  |  |
|  |  | 130 |  |  |  | 135 |  |  |  |  | 140 |  |  |  |  |

( 2 ) INFORMATION FOR SEQ ID NO:2:

( i ) SEQUENCE CHARACTERISTICS:
  ( A ) LENGTH: 423
  ( B ) TYPE: nucleic acid
  ( C ) STRANDEDNESS: single
  ( D ) TOPOLOGY: linear ( i i ) MOLECULE TYPE:
  ( A ) DESCRIPTION: Genomic DNA ( i i i ) HYPOTHETICAL: No ( i v ) ANTI-SENSE: No ( i x ) FEATURE:
  ( A ) NAME/KEY:
  ( B ) LOCATION:
  ( C ) IDENTIFICATION METHOD:
  ( D ) OTHER INFORMATION: This sequence can be
   found on page 5, lines 3-13, in the
   application, as filed.

( x ) PUBLICATION INFORMATION:
  ( A ) AUTHORS:
  ( B ) TITLE:
  ( C ) JOURNAL:
  ( D ) VOLUME:
  ( E ) ISSUE:
  ( F ) PAGES:
  ( G ) DATE:
  ( H ) DOCUMENT NUMBER:
  ( I ) FILING DATE:
  ( J ) PUBLICATION DATE:
  ( K ) RELEVANT RESIDUES IN SEQ ID NO: 1-423

( x i ) SEQUENCE DESCRIPTION: SEQ ID NO:2:

| GCG | GCC | GTC | CAG | AGC | GGC | GCC | GGC | GAC | TAC | CTG | CTG | GGC | 39 |
| ATC | AAG | CGG | CTG | CGG | CGG | CTC | TAC | TGC | AAC | GTG | GGC | ATC | 78 |
| GGC | TTC | CAC | CTC | CAG | GCG | CTC | CCC | GAC | GGC | CGC | ATC | GGC | 117 |
| GGC | GCG | CAC | GCG | GAC | ACC | CGC | GAC | AGC | CTG | CTG | GAG | CTC | 156 |
| TCG | CCC | GTG | GAG | CGG | GGC | GTG | GTG | AGC | ATC | TTC | GGC | GTG | 195 |
| GCC | AGC | CGG | TTC | TTC | GTG | GCC | ATG | AGC | AGC | AAG | GGC | AAG | 234 |
| CTC | TAT | GGC | TCG | CCC | TTC | TTC | ACC | GAT | GAG | TGC | ACG | TTC | 273 |
| AAG | GAG | ATT | CTC | CTT | CCC | AAC | AAC | TAC | AAC | GCC | TAC | GAG | 312 |
| TCC | TAC | AAG | TAC | CCC | GGC | ATG | TTC | ATC | GCC | CTG | AGC | AAG | 351 |

```
AAT  GGG  AAG  ACC  AAG  AAG  GGG  AAC  CGA  GTG  TCG  CCC  ACC              390

ATG  AAG  GTC  ACC  CAC  TTC  CTC  CCC  AGG  CTG  TGA                         423
```

( 2 ) INFORMATION FOR SEQ ID NO:3:

( i ) SEQUENCE CHARACTERISTICS:
            ( A ) LENGTH: 145
            ( B ) TYPE: amino acid
            ( C ) STRANDEDNESS: single
            ( D ) TOPOLOGY: linear ( i i ) MOLECULE TYPE:
            ( A ) DESCRIPTION: Protein ( i x ) FEATURE:
            ( A ) NAME/KEY:
            ( B ) LOCATION:
            ( C ) IDENTIFICATION METHOD:
            ( D ) OTHER INFORMATION: This sequence,
                   corresponding to bovine basic fibroblast
                   growth factor, can be found in Table 1,
                   page 9, lines 9, 14, and 19, in the
                   application, as filed.

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO: 1-145

( x i ) SEQUENCE DESCRIPTION: SEQ ID NO:3:

```
Pro  Ala  Leu  Pro  Glu  Asp  Gly  Gly  Ser  Gly  Ala  Phe  Pro  Pro  Gly  His
 1              5                        10                         15

Phe  Lys  Asp  Pro  Lys  Arg  Leu  Tyr  Cys  Lys  Asn  Gly  Gly  Phe  Phe  Leu
                20                    25                      30

Arg  Ile  His  Pro  Asp  Gly  Arg  Val  Asp  Gly  Val  Arg  Glu  Lys  Ser  Asp
          35                        40                    45

Pro  His  Ile  Lys  Leu  Gln  Leu  Gln  Ala  Glu  Glu  Arg  Gly  Val  Val  Ser
     50                   55                        60

Ile  Lys  Gly  Val  Cys  Ala  Asn  Arg  Tyr  Leu  Ala  Met  Lys  Glu  Asp  Gly
 65                    70                        75                          80

Arg  Leu  Leu  Ala  Ser  Lys  Cys  Val  Thr  Asp  Glu  Cys  Phe  Phe  Phe  Glu
                    85                        90                         95

Arg  Leu  Glu  Ser  Asn  Asn  Tyr  Asn  Thr  Tyr  Arg  Ser  Arg  Lys  Tyr  Ser
               100                       105                    110

Ser  Trp  Tyr  Val  Ala  Leu  Lys  Arg  Thr  Gly  Gln  Tyr  Lys  Leu  Gly  Pro
          115                    120                      125

Lys  Thr  Pro  Gly  Gln  Lys  Ala  Ile  Leu  Phe  Leu  Pro  Met  Ser  Ala  Lys
     130                        135                    140

Ser
145
```

( 2 ) INFORMATION FOR SEQ ID NO:4:

( i ) SEQUENCE CHARACTERISTICS:
            ( A ) LENGTH: 140
            ( B ) TYPE: amino acid
            ( C ) STRANDEDNESS: single
            ( D ) TOPOLOGY: linear ( i i ) MOLECULE TYPE:
    ( A ) DESCRIPTION: Protein ( i i i ) HYPOTHETICAL: No ( i v ) ANTI-SENSE: No ( i x ) FEATURE:
    ( A ) NAME/KEY:
    ( B ) LOCATION:
    ( C ) IDENTIFICATION METHOD:
    ( D ) OTHER INFORMATION: This sequence,
         corresponding to bovine acid fibroblast
         growth factor, can be found in Table 1,
         page 9, lines 26, 31, and 36 in the
         specification, as filed.

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO: 1-140

( x i ) SEQUENCE DESCRIPTION: SEQ ID NO:4:

| Phe | Asn | Leu | Pro | Leu | Gly | Asn | Tyr | Lys | Lys | Pro | Lys | Leu | Leu | Tyr | Cys |
|---|---|---|---|---|---|---|---|---|---|---|---|---|---|---|---|
| 1 | | | | 5 | | | | | 10 | | | | | 15 | |
| Ser | Asn | Gly | Gly | Tyr | Phe | Leu | Arg | Ile | Leu | Pro | Asp | Gly | Thr | Val | Asp |
| | | | 20 | | | | | 25 | | | | | 30 | | |
| Gly | Thr | Lys | Asp | Arg | Ser | Asp | Gln | His | Ile | Gln | Leu | Gln | Leu | Cys | Ala |
| | | 35 | | | | | 40 | | | | | 45 | | | |
| Glu | Ser | Ile | Gly | Glu | Val | Tyr | Ile | Lys | Ser | Thr | Glu | Thr | Gly | Gln | Phe |
| | 50 | | | | | 55 | | | | | 60 | | | | |
| Leu | Ala | Met | Asp | Thr | Asp | Gly | Leu | Leu | Tyr | Gly | Ser | Gln | Thr | Pro | Asn |
| 65 | | | | | 70 | | | | 75 | | | | | | 80 |
| Glu | Glu | Cys | Leu | Phe | Leu | Glu | Arg | Leu | Glu | Glu | Asn | His | Tyr | Asn | Thr |
| | | | | 85 | | | | | 90 | | | | | 95 | |
| Tyr | Ile | Ser | Lys | Lys | His | Ala | Glu | Lys | His | Trp | Phe | Val | Gly | Leu | Lys |
| | | | 100 | | | | | 105 | | | | | 110 | | |
| Lys | Asn | Gly | Arg | Ser | Lys | Leu | Gly | Pro | Arg | Thr | His | Phe | Gly | Gln | Lys |
| | | 115 | | | | | 120 | | | | | 125 | | | |
| Ala | Ile | Leu | Phe | Leu | Pro | Leu | Pro | Val | Ser | Ser | Asp | | | | |
| | 130 | | | | | 135 | | | | | 140 | | | | |

( 2 ) INFORMATION FOR SEQ ID NO:5:

( i ) SEQUENCE CHARACTERISTICS:
    ( A ) LENGTH: 423
    ( B ) TYPE: nucleic acid
    ( C ) STRANDEDNESS: single
    ( D ) TOPOLOGY: linear ( i i ) MOLECULE TYPE:
    ( A ) DESCRIPTION: Genomic DNA ( i x ) FEATURE:
    ( A ) NAME/KEY:
    ( B ) LOCATION:
    ( C ) IDENTIFICATION METHOD:
    ( D ) OTHER INFORMATION: This sequence
         corresponds to K-FGF-140 and can be
         found on page 11, lines 39-47 and page
         12, lines 1-31, in the application, as
         filed.

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO: 1-423

( x i ) SEQUENCE DESCRIPTION: SEQ ID NO:5:

| GCG | GCC | GTC | CAG | AGC | GGC | GCC | GGC | GAC | TAC | CTG | CTG | GGC | 39 |
| Ala | Ala | Val | Gln | Ser | Gly | Ala | Gly | Asp | Tyr | Leu | Leu | Gly | |
| 1 | | | | 5 | | | | | 10 | | | | |

| ATC | AAG | CGG | CTG | CGG | CGG | CTC | TAC | TGC | AAC | GTG | GGC | ATC | 78 |
| Ile | Lys | Arg | Leu | Arg | Arg | Leu | Tyr | Cys | Asn | Val | Gly | Ile | |
| | 15 | | | | | 20 | | | | | 25 | | |

| GGC | TTC | CAC | CTC | CAG | GCG | CTC | CCC | GAC | GGC | CGC | ATC | GGC | 117 |
| Gly | Phe | His | Leu | Gln | Ala | Leu | Pro | Asp | Gly | Arg | Ile | Gly | |
| | | | 30 | | | | | 35 | | | | | |

| GGC | GCG | CAC | GCG | GAC | ACC | CGC | GAC | AGC | CTG | CTG | GAG | CTC | 156 |
| Gly | Ala | His | Ala | Asp | Thr | Arg | Asp | Ser | Leu | Leu | Glu | Leu | |
| 40 | | | | 45 | | | | | 50 | | | | |

| TCG | CCC | GTG | GAG | CGG | GGC | GTG | GTG | AGC | ATC | TTC | GGC | GTG | 195 |
| Ser | Pro | Val | Glu | Arg | Gly | Val | Val | Ser | Ile | Phe | Gly | Val | |
| | | 55 | | | | | 60 | | | | | 65 | |

| GCC | AGC | CGG | TTC | TTC | GTG | GCC | ATG | AGC | AGC | AAG | GGC | AAG | 234 |
| Ala | Ser | Arg | Phe | Phe | Val | Ala | Met | Ser | Ser | Lys | Gly | Lys | |
| | | | | 70 | | | | | 75 | | | | |

| CTC | TAT | GGC | TCG | CCC | TTC | TTC | ACC | GAT | GAG | TGC | ACG | TTC | 273 |
| Leu | Tyr | Gly | Ser | Pro | Phe | Phe | Thr | Asp | Glu | Cys | Thr | Phe | |
| | 80 | | | | | 85 | | | | | 90 | | |

| AAG | GAG | ATT | CTC | CTT | CCC | AAC | AAC | TAC | AAC | GCC | TAC | GAG | 312 |
| Lys | Glu | Ile | Leu | Leu | Pro | Asn | Asn | Tyr | Asn | Ala | Tyr | Glu | |
| | | | 95 | | | | | 100 | | | | | |

| TCC | TAC | AAG | TAC | CCC | GGC | ATG | TTC | ATC | GCC | CTG | AGC | AAG | 351 |
| Ser | Tyr | Lys | Tyr | Pro | Gly | Met | Phe | Ile | Ala | Leu | Ser | Lys | |
| 105 | | | | | 110 | | | | | 115 | | | |

| AAT | GGG | AAG | ACC | AAG | AAG | GGG | AAC | CGA | GTG | TCG | CCC | ACC | 390 |
| Asn | Gly | Lys | Thr | Lys | Lys | Gly | Asn | Arg | Val | Ser | Pro | Thr | |
| | | 120 | | | | | 125 | | | | | 130 | |

| ATG | AAG | GTC | ACC | CAC | TTC | CTC | CCC | AGG | CTG | TGA | | | 423 |
| Met | Lys | Val | Thr | His | Phe | Leu | Pro | Arg | Leu | | | | |
| | | | | 135 | | | | | 140 | | | | |

( 2 ) INFORMATION FOR SEQ ID NO:6:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( i i ) FEATURE:
        ( A ) OTHER INFORMATION: This sequence can be
          found on page 15, line 9, in the
          application as filed.

( i i i ) SEQUENCE DESCRIPTION: SEQ ID NO:6:

| GCG | GCC | GTC | CAG | AGC | GGC | GCC | GGC | GAC | | 27 |

( 2 ) INFORMATION FOR SEQ ID NO:7:

(i) SEQUENCE CHARACTERISTICS:
  (A) LENGTH: 30
  (B) TYPE: nucleic acid
  (C) STRANDEDNESS: single
  (D) TOPOLOGY: linear (ii) FEATURE:
  (A) OTHER INFORMATION: This sequence can be found on page 15, line 10, in the application as filed.

(iii) SEQUENCE DESCRIPTION: SEQ ID NO:7:

ATG GCA GCA GTT CAA TCA GGA GCA GGC GAC          30

(2) INFORMATION FOR SEQ ID NO:8:

(i) SEQUENCE CHARACTERISTICS:
    (A) LENGTH: 10
    (B) TYPE: amino acid
    (C) STRANDEDNESS: single
    (D) TOPOLOGY: linear (ii) FEATURE:
    (A) OTHER INFORMATION: This sequence can be found on page 15, line 11, in the application as filed.

(iii) SEQUENCE DESCRIPTION: SEQ ID NO:8:

Met Ala Ala Val Gln Ser Gly Ala Gly Asp
 1               5                   10